(12) United States Patent
van't Hooft et al.

(10) Patent No.: US 10,933,255 B2
(45) Date of Patent: Mar. 2, 2021

(54) TRANSPORT CABLE AND SOURCE CAPSULE WITH SAFE CONNECTING CONSTRUCTION FOR INTERNALLY IRRADIATING PATIENTS

(75) Inventors: Eric van't Hooft, Brasschaat (BE); Libbe van Zwol, Veenendaal (NL)

(73) Assignee: Nucletron Operations B.V., Veenendaal (NL)

( * ) Notice: Subject to any disclaimer, the term of this patent is extended or adjusted under 35 U.S.C. 154(b) by 1401 days.

(21) Appl. No.: 11/876,419

(22) Filed: Oct. 22, 2007

(65) Prior Publication Data

US 2008/0119687 A1 May 22, 2008

(30) Foreign Application Priority Data

Oct. 20, 2006 (NL) .................................... 1032714

(51) Int. Cl.
*A61N 5/10* (2006.01)
*A61M 36/04* (2006.01)

(52) U.S. Cl.
CPC .... *A61N 5/1027* (2013.01); *A61N 2005/1025* (2013.01)

(58) Field of Classification Search
CPC ......... A61N 2005/1025; A61N 5/1027; A61M 2025/09075; A61M 2025/0915; A61M 2025/09091; A61M 25/09–091; A61M 2025/09008–09191
USPC .................................................. 600/1–8, 585
See application file for complete search history.

(56) References Cited

U.S. PATENT DOCUMENTS

| | | | | |
|---|---|---|---|---|
| 2,062,886 A * | 12/1936 | Jensen | ................. | B23K 1/0008 403/265 |
| 4,819,618 A * | 4/1989 | Liprie | .............................. | 600/7 |
| 4,917,103 A * | 4/1990 | Gambale | ........... | A61M 25/0169 600/434 |
| 5,137,013 A * | 8/1992 | Chiba | .................... | A61B 17/29 604/524 |
| 5,141,487 A * | 8/1992 | Liprie | .............................. | 600/7 |
| 5,282,781 A | 2/1994 | Liprie | | |
| 5,924,974 A | 7/1999 | Löffler | | |
| 6,193,706 B1 * | 2/2001 | Thorud et al. | ................. | 604/533 |
| 6,196,964 B1 * | 3/2001 | Loffler et al. | ..................... | 600/7 |
| 6,203,485 B1 * | 3/2001 | Urick | .................. | 600/3 |
| 6,352,500 B1 * | 3/2002 | Halpern | ............................ | 600/3 |
| 6,659,933 B2 * | 12/2003 | Asano | .................. | 600/3 |
| 6,709,381 B2 * | 3/2004 | Munro, III | ........................ | 600/3 |
| 2003/0069521 A1 * | 4/2003 | Reynolds | .............. | A61L 31/022 600/585 |

(Continued)

FOREIGN PATENT DOCUMENTS

DE 19758234 C2 7/1997
EP 0 367 340 B1 5/1990
(Continued)

*Primary Examiner* — Catherine B Kuhlman
(74) *Attorney, Agent, or Firm* — Leydig, Voit & Mayer, Ltd.

(57) ABSTRACT

A source guide apparatus for brachytherapy application, wherein the source guide apparatus is provided with a source capsule, a guidewire for moving the source capsule through a catheter, a mechanical connection between the guidewire and the source capsule, wherein the source guide apparatus is provided with a sleeve which is attached on the capsule, wherein the sleeve envelops at least a part of the mechanical connection.

13 Claims, 2 Drawing Sheets

(56) References Cited

U.S. PATENT DOCUMENTS

2004/0106878 A1\* 6/2004 Skujins ............... A61M 25/09
                                                600/585
2004/0116767 A1\* 6/2004 Lebovic et al. ............... 600/7
2006/0058568 A1 3/2006 Gross et al.

FOREIGN PATENT DOCUMENTS

| WO | WO 94/23789 A1 | 10/1994 |
| WO | WO 98/01186 A1 | 1/1998 |
| WO | WO 99/15234 A1 | 4/1999 |
| WO | WO 99/15235 A1 | 4/1999 |
| WO | WO 00/43066 A1 | 7/2000 |

\* cited by examiner

TRANSPORT CABLE AND SOURCE CAPSULE WITH SAFE CONNECTING CONSTRUCTION FOR INTERNALLY IRRADIATING PATIENTS

AREA OF THE INVENTION

The invention relates to a source guide apparatus for brachytherapy applications.

BACKGROUND

U.S. Pat. No. 6,196,964 describes a source guide apparatus for brachytherapy application. The American patent describes an assembly of a capsule for brachytherapy and a guidewire. The guidewire is connected with the capsule via a flexible adapter which is thinner compared to the guidewire, while the adapter and the capsule are attached to each other by means of a weld. In use, first a catheter is provided in the body of a patient and then the capsule is introduced into the body via a catheter with the aid of a remotely controllable apparatus.

US2006/0058568 discloses a source guide apparatus for brachytherapy application provided with a source capsule a guidewire for moving the source capsule through a catheter and a sleeve that is attached on the capsule at least partly enveloping the guidewire. The sleeve provides a crimp connection to connect the guidewire to the capsule.

SUMMARY OF THE INVENTION

The disclosed apparatus addresses potential shortcomings in the above-identified apparatuses, including: a vulnerable transition area, arising from a weld, present in the adaptor of the apparatus disclosed in the U.S. Pat. No. 6,196,964; and reduced flexibility in a crimp region in the source guide apparatus disclosed in US Published App. 2006/0058568.

According to one aspect, the source guide apparatus is provided with a source capsule, a guidewire for moving the source capsule through a catheter, and a sleeve that is attached on the capsule at least partly enveloping the guidewire, wherein a mechanical connection is provided between an end face of the guidewire and a face of the source capsule, the sleeve extending away from the mechanical connection to stabilize the mechanical connection from deformations of the guidewire.

BRIEF DESCRIPTION OF THE DRAWINGS

This aspect and other aspects will now be described in more detail by way of example with reference to the following drawings, in which.

DETAILED DESCRIPTION OF THE DRAWINGS

Figure 1:
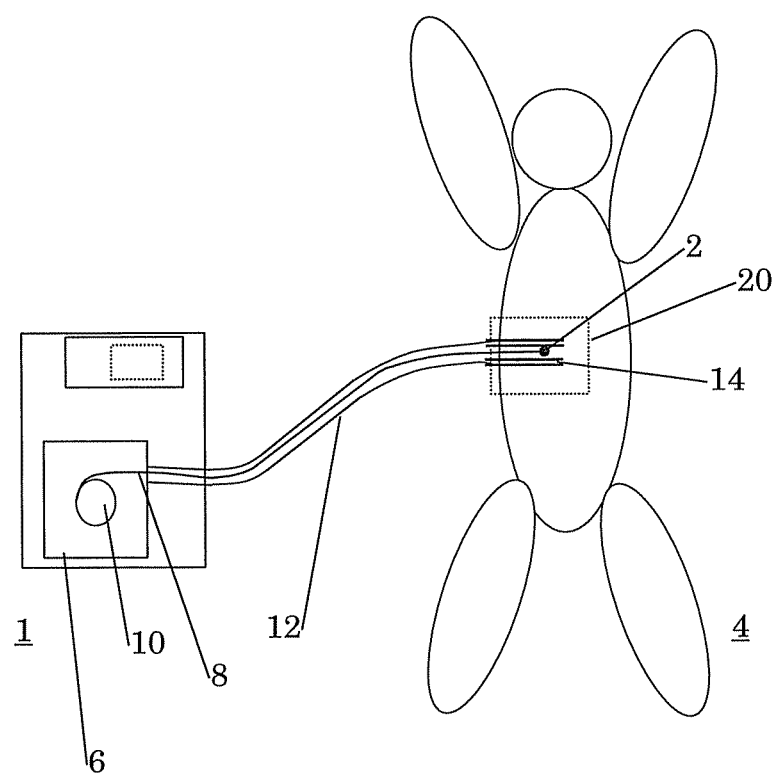
FIG. 1 shows a system in which the source guide apparatus according to the invention can be used.

FIG. 1 shows a schematic representation of a system in which the source guide apparatus according to the invention can be used. In the Figure, a system 1 is shown for guiding a radiation source 2 in a human body 4 for brachytherapy applications. The system 1 comprises a shielding housing 6, in which the radiation source 2 is stored, if not in use. In the Figure, a condition is shown where the source 2 is taken from the housing 6 and emits radiation in the human body 4. This, for instance, takes place by guiding the source 2 via a guidewire 8, which guides the source 2 into and out of the housing 6 by means of a movement mechanism 10, via a guide tube 12. The guide tube 12 connects to a catheter 14 inserted into the body 4, to the positions to be irradiated. Although the catheter 14 defines a straight path in FIG. 1, it is also possible for the catheter to define a curved path.

The system 1 defines a treatment area 20 for the treatment of tissues in the human body 4. In this treatment area 20, predetermined positions, the so-called dwell positions, are taken by the source 2 to achieve an optimal irradiation result for the body 4 according to a predetermined time schedule. To this end, the system 1 can keep the source 2 in a number of fixed, presettable positions in the treatment area 20, which are, for instance, always spaced 1 mm apart, while the movement mechanism 10 comprises, for instance, a stepping motor to guide the source 2 through in a stepwise manner.

Figure 2:
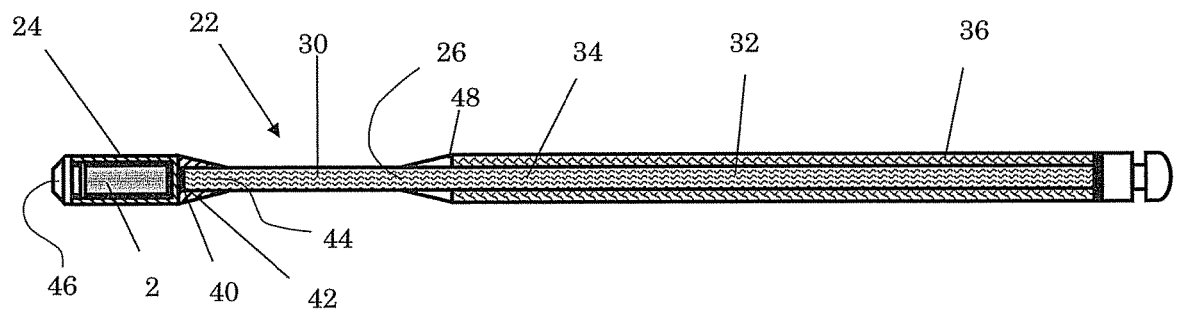
FIG. 2 shows a longitudinal section of a first embodiment of the source guide apparatus according to the invention.

As FIG. 2 shows, the radiation source 2 is included in a source guide apparatus 22 for brachytherapy application. The source guide apparatus 22 is provided with a source capsule 24 and a guidewire 26 for moving the source capsule 24 through the catheter 14 (see FIG. 1). The guidewire 26 is provided with a flexible portion 30 which has a higher flexibility in a transverse direction of the guidewire than a remaining portion 32 of the guidewire 26. As the Figures show, in the embodiments shown, the flexible portion 30 is located between the source capsule 24 and the remaining portion 32. Due to the flexible portion 30, the source guide apparatus 22 can have a flexible design near the source capsule 24, which is potentially favorable for making the source capsule 24 follow curved bends in the catheter 14.

In this embodiment, the guidewire 26 further comprises an inner cable 34, a casing 36 around the inner cable 34, and leaves a part/section of the inner cable 34 clear in a longitudinal direction of the guidewire 26 for forming the flexible portion 30 of the guidewire 26. In this embodiment of the source guide apparatus, the casing 36 is built up from filaments (not shown in the Figures). The flexible portion 30 extends from the source capsule 24 to the casing 36. In this embodiment, the source guide apparatus 22 comprises a weld 40 between an end face of the capsule 24 and an end face of the guidewire 26 for forming a mechanical connection between the capsule 24 and the guidewire 26. Instead of the weld 40, another suitable connection may be chosen as well, such as a form-closed connection or a glue connection. Further, a part of the guidewire 26 may be clamped in the sleeve 42 for forming the mechanical connection.

The guidewire 26 further comprises an inner cable 30 and the source guide apparatus 22 is provided with a sleeve 42 which is attached on the capsule 24. In this embodiment, the sleeve 42 envelops a part of the inner cable 30 and the weld 40.

In manufacture of the source guide apparatus 22, the sleeve 42 may, for instance, be slid on the guidewire 26 first. Then the guidewire 26 may be welded against the capsule, after which the sleeve 42 is attached on the capsule, for instance by means of welding, but optionally by means of gluing or clamping.

It is also possible for the sleeve 42 to be slid on the guidewire 26 first and be attached on an end thereof by means of glue, a form-closed connection or another suitable manner of attachment, after which the guidewire 26 and the sleeve 42 are together attached on the source capsule 24 with the aid of the weld 40. In the latter case, the sleeve 42 can relieve the thermal load on the guidewire 26 upon providing the weld 40.

According to another manner of manufacturing the source guide apparatus 22, the sleeve 42 is attached on the capsule 24, after which the guidewire 26 is attached on the capsule 24 by the sleeve 42 in a suitable manner.

With still another manner of manufacturing the source guide apparatus 22, the sleeve 42 is an integral part of the capsule 24, and attaching the guidewire 26 on the capsule 24 is sufficient.

Further, in the inner cable 34, an annealed portion 44 is present as a result of providing the weld 40. Preferably, the sleeve 42 has such a size and the sleeve 42 is in such a position that this annealed portion 44 is wholly or virtually wholly enveloped by the sleeve 42. Thus, the usually vulnerable, annealed portion 44 of the guidewire 26 is shielded from mechanical load in the transverse direction, so that breaking at the location of the annealed portion 44 is prevented to a great extent by the sleeve fixing transverse mechanical loads and extending over a distance away from the annealed portion 44 towards the flexible part of the guidewire 26.

Figure 3:
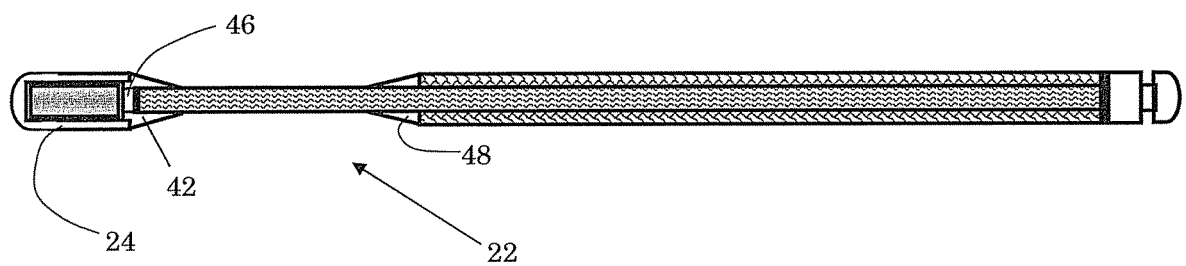
FIG. 3 shows a modification of the first embodiment of the source guide apparatus of FIG. 2.

At a distal end of the capsule 24, the capsule 24 is provided with an opening via which the radiation source 2 is introduced into the capsule 24. In FIG. 1, the capsule 24 is closed off by means of a lid 46 placed on the distal end of the capsule 24. However, the lid 46 from FIG. 2 may be replaced by a fixed wall. The opening and the lid 46 of the capsule 24 may then, for instance, be located on the proximal side of the capsule 24, as for instance shown in FIG. 3 depicting a modified version of the embodiment depicted in FIG. 2.

Near the flexible portion 30, an end of the casing 36 is located which is provided with a casing sleeve 48 attached on the casing 36. The casing sleeve 48 envelops a part of the flexible portion 30 located near the casing 36. Because, in this embodiment, the casing sleeve 48 is attached on the end of the casing 36, in this example by means of a second weld, the filaments of the casing 36 are prevented from fraying. Further, near the casing sleeve 48, the inner cable 34 is formed as one continuous element. This can have the advantage that the source guide apparatus 22 is stronger than source guide apparatuses where, in a similar inner cable, there is a weld near the sleeve.

In this embodiment of the source guide apparatus 22, as a casing sleeve 48, a sleeve of the same type as the sleeve 42 attached on the capsule 24 is chosen. However, it is also possible to use another type of sleeve. Thus, a short sleeve can be used, which can keep the transition between the casing 36 and the flexible portion 30 as short as possible. This may be desirable, for instance if the flexible portion is short and the sleeve 42 needs to limit its flexibility as little as possible. However, it is also possible to choose a longer sleeve, for instance, to prevent a bend of the guidewire near the transition between the remaining portion 32 and the flexible portion.

Figure 4:
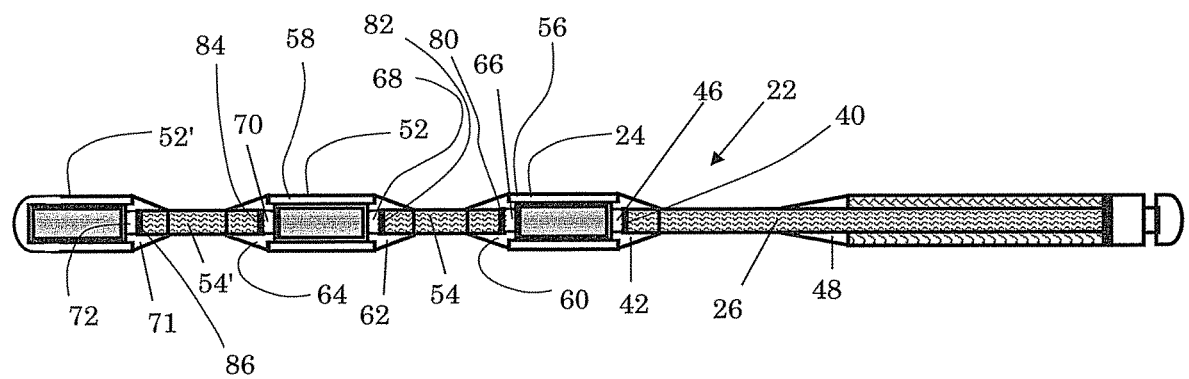
FIG. 4 shows a longitudinal section of a second embodiment of the source guide apparatus according to the invention.

With reference to FIG. 4, a second embodiment is described. This embodiment of the source guide apparatus is, in addition to the source capsule 24, provided with two further source capsules 52, 52' and two further guidewires 54, 54'. The source capsule 24 and the first further source capsule 52 may each be provided with a cylindrical body 56, 58 with a sleeve 42 and/or a further sleeve 60, 62, 64 at both a proximal and a distal end of the respective body 56, 58. In each of these sleeves 42, 60, 62, 64, a lid 46 or a further lid 66, 68, 70 is included for closing off the cylindrical body. The second further source capsule 52' is, in this embodiment, provided with a cylindrical body closed on one side with a further sleeve 71 and a further lid 72.

Further, between the source capsule 24 and the further guidewire 54, a mechanical connection, in this embodiment a further weld 80, is provided. Also, further welds 82, 84, 86 are provided between the first further source capsule 52 and first further guidewire 54, between the first further source capsule 52 and second guidewire 54' and between the second further source capsule 52' and the second guidewire 54', respectively, as can also be seen in FIG. 4.

Since, in this embodiment, multiple source capsules 24, 52, 52' are provided, it is possible to irradiate from multiple positions. So, irradiating the tissue from multiple dwell positions can take place simultaneously and without the guidewire moving the source capsules.

The above described embodiments are illustrative, and thus the invention is not intended to be limited to those embodiments. Rather, the scope of the present invention is defined according to the claims appended hereto in view of the exemplary embodiments provided herein.

What is claimed is:

1. A source guide apparatus for brachytherapy application, wherein the source guide apparatus comprises:
    a source capsule;
    a guidewire arranged for moving the source capsule through a catheter, the guidewire comprising;
        art inner cable comprising;
            a first portion,
            a second portion, and
            a third portion; and
        a casing:
    and
    a capsule sleeve,
    wherein a mechanical connection is provided between the guidewire and the source capsule by welding an end face of the third portion and a face of the source capsule, the welding resulting in an annealed part of the third portion,
    wherein the casing covers the first portion of the inner cable to form a relatively inflexible length of the guidewire,
    wherein the second portion of the inner cable is not covered by the casing to form a relatively flexible length of the guidewire in comparison to the relatively inflexible length, and
    wherein the capsule sleeve is configured to extend over at least the mechanical connection and the annealed part of the third portion to shield the annealed part from mechanical load in a transverse direction during use of the source guide apparatus.

2. A source guide apparatus according to claim 1, wherein the capsule sleeve is tubular.

3. A source guide apparatus according to claim 1, wherein the capsule sleeve wholly envelops the mechanical connection.

4. A source guide apparatus according, to claim 1, wherein a part of the guidewire is clamped in the capsule sleeve for forming an additional mechanical connection.

5. A source guide apparatus according to claim 1, wherein the source guide apparatus is provided with at least one further capsule and a further guidewire, wherein the further guidewire is included between the capsules, wherein the source guide apparatus is provided with a first further mechanical connection between the capsule and the further guidewire and a second further mechanical connection between the further capsule and the further guidewire.

6. A source guide apparatus according to claim 5, wherein the source guide apparatus is provided with a further capsule sleeve which is attached on the capsule or on the further capsule.

7. A source guide apparatus according to claim 6, wherein the further capsule sleeve envelops at least a part of the further mechanical connection.

8. A source guide apparatus according to claim 6, wherein at least one of the first or the second further mechanical connection comprises a further weld and wherein the further capsule sleeve at least partly envelops the further weld.

9. A source guide apparatus according to claim 8, wherein the further capsule sleeve at least nearly envelops the further weld.

10. A source guide apparatus according to claim 1, wherein an end of the casing located near the flexible portion is provided with a casing sleeve attached on the casing which envelops a part of the flexible portion located near the casing and wherein the inner cable is, at least near the casing sleeve, formed by one continuous element.

11. A source guide apparatus according to claim 1 wherein a casing sleeve is attached at an end of the casing proximate the second portion of the inner cable, and wherein the first portion of the inner cable is, at least near the casing sleeve, formed by one continuous element.

12. A source guide apparatus according to claim 11, wherein the casing sleeve is attached to the casing by a weld.

13. A source guide apparatus according to claim 1, wherein the inner cable consists of a single continuous element.

\* \* \* \* \*